United States Patent [19]

Goldsmith et al.

[11] Patent Number: 5,228,852
[45] Date of Patent: Jul. 20, 1993

[54] HANDPIECE ASSEMBLY FOR A DENTAL LASER

[75] Inventors: Daniel S. Goldsmith, West Bloomfield; William S. Parker, Ann Arbor; Michael P. Howell, Bloomfield Hills; Terry D. Myers, Farmington Hills; William D. Myers, Birmingham, all of Mich.

[73] Assignee: American Dental Laser, Inc., Troy, Mich.

[21] Appl. No.: 861,088

[22] Filed: Mar. 31, 1992

[51] Int. Cl.$^5$ ................................................ A61C 3/00
[52] U.S. Cl. ..................................... 433/141; 433/229
[58] Field of Search .................... 433/29, 141, 229; 604/15, 16

[56] References Cited

U.S. PATENT DOCUMENTS

| | | | |
|---|---|---|---|
| 3,834,391 | 9/1974 | Block | 128/303.1 |
| 3,897,134 | 7/1975 | Serivo et al. | 350/96 B |
| 4,522,594 | 6/1985 | Stark et al. | 433/141 |
| 4,723,825 | 2/1988 | Herold | 350/96.1 |
| 5,125,058 | 6/1992 | Tenerz et al. | 385/66 |

Primary Examiner—John J. Wilson
Assistant Examiner—Cindy A. Cherichetti
Attorney, Agent, or Firm—Gifford, Groh, Sprinkle, Patmore and Anderson

[57] ABSTRACT

A handpiece assembly is disclosed for use with a dental laser assembly of the type having a laser and an elongated optical fiber assembly. The optical fiber assembly has a proximal end which receives radiation from the laser and a distal end which delivers the laser radiation to a target site. The handpiece assembly includes an elongated handpiece which is dimensioned to be held in a human hand. A longitudinal throughbore is formed in the handpiece and is dimensioned to slidably receive the optical fiber assembly so that the distal end of the optical fiber assembly extends outwardly from one end of the handpiece. A locking assembly removably locks the other end of the handpiece against longitudinal movement to the optical fiber assembly. Furthermore, the entire handpiece assembly is discarded after use on a single patient to prevent disease transmission by the handpiece.

20 Claims, 3 Drawing Sheets

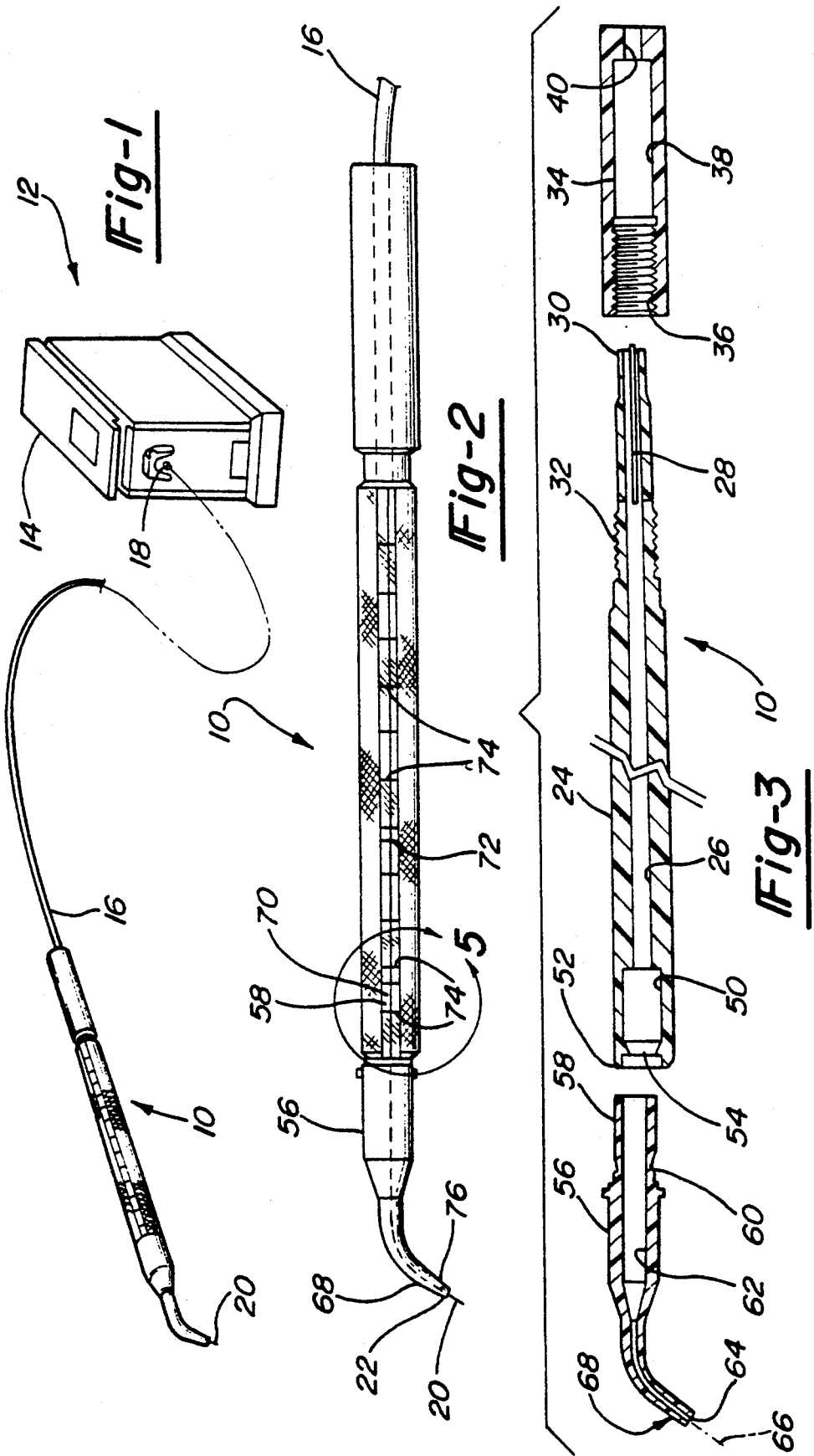

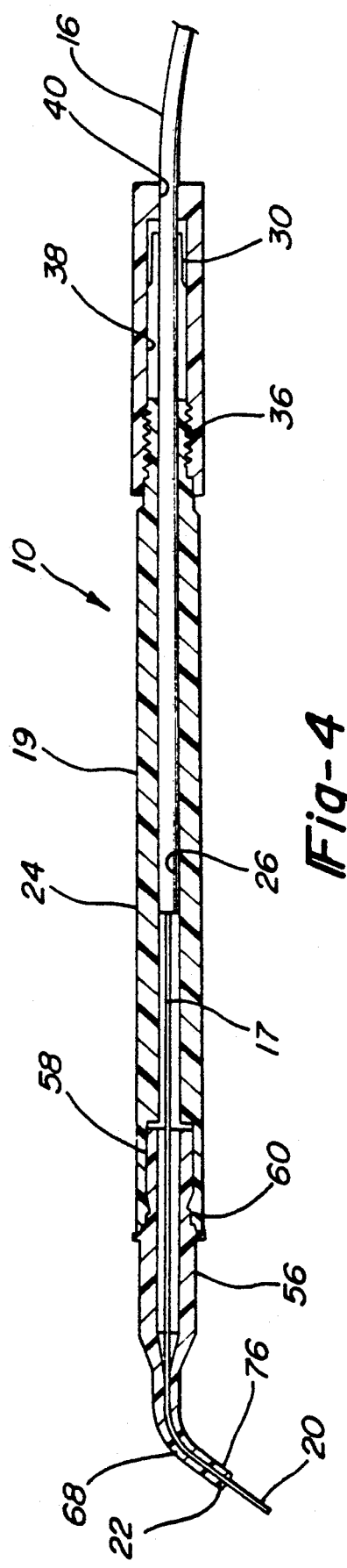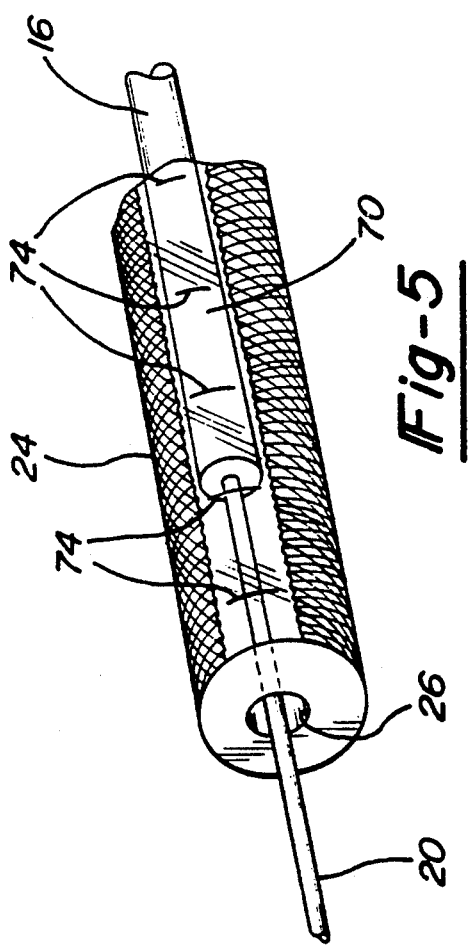

HANDPIECE ASSEMBLY FOR A DENTAL LASER

BACKGROUND OF THE INVENTION

I. Field of the Invention

The present invention relates generally to dental instruments and, more particularly, to a handpiece for a dental laser. II. Description of the Prior Art In dental laser assemblies the laser is typically contained within a housing separate from the patient. An elongated optical fiber assembly has a proximal end connected to the laser housing which receives the radiation from the laser. The opposite or distal end of the fiber optic assembly is used to deliver the laser radiation to the target site. The optical fiber assembly is flexible in nature.

Previously, a handpiece has been connected to the distal end of the optical fiber assembly. The dentist would then grasp the handpiece and aim the distal end of the fiber optic assembly toward the target site.

In order to prevent the transmission of diseases from one patient to the next, it has been necessary for the dentist to completely sterilize the dental handpiece between each patient use. Such sterilization is time consuming, and therefore, expensive and undesirable for the dentist.

SUMMARY OF THE PRESENT INVENTION

The present invention provides a device which overcomes al of the above mentioned disadvantages of the previously known devices.

In brief, the present invention comprises an elongated handpiece which is dimensioned to be held in a human hand. The handpiece includes a longitudinal throughbore which is dimensioned to slidably receive the optical fiber assembly so that the distal end of the optical fiber in the optical fiber assembly extends outwardly from one end of the handpiece.

Means are then provided for locking the other end of the handpiece against longitudinal movement to the optical fiber assembly. In the preferred form of the invention, one or more longitudinally extending slots are formed in the handpiece at its other end while a lock nut threadably engages an externally threaded portion at the other end of the handpiece. Thus, as the nut is tightened, the nut compresses the slotted end of the handpiece against the optical fiber assembly thereby frictionally locking the optical fiber assembly and handpiece together.

Preferably, the handpiece includes both an elongated body and a cannula, both of which have longitudinally extending throughbores. The cannula and body are frictionally locked together so that their throughbores register with each other. In addition, the locking assembly of the cannula and body, while permitting the body and cannula to be locked together, prevent detachment of the cannula from the body without destruction or severe damage to the handpiece.

The entire handpiece is constructed from an inexpensive plastic material, such as polypropylene. Such material, furthermore, cannot be adequately sterilized by the dentist. Thus, after each patient use, the lock nut is loosened, the handpiece removed from the optical fiber and discarded, and a new sterilized handpiece is then attached to the optical fiber assembly in the above described fashion. Consequently, any transmission of diseases through the handpiece from one patient to another is completely avoided.

BRIEF DESCRIPTION OF THE DRAWINGS

A better understanding of the present invention will be had upon reference to the following detailed description, when read in conjunction with the accompanying drawings, wherein like reference numerals refer to like parts throughout the several views, and in which:

FIG. 1 is a perspective view illustrating a preferred embodiment of the present invention used in connection with a dental laser assembly;

FIG. 2 is a side view of the preferred embodiment of the handpiece of the present invention;

FIG. 3 is an exploded longitudinal sectional view illustrating the preferred embodiment of the handpiece of the present invention;

FIG. 4 is a longitudinal section view illustrating the assembled handpiece of the present invention;

FIG. 5 is a view of circle 5—5 in FIG. 2 and enlarged for clarity;

DETAILED DESCRIPTION OF A PREFERRED EMBODIMENT OF THE PRESENT INVENTION

Figure 6:
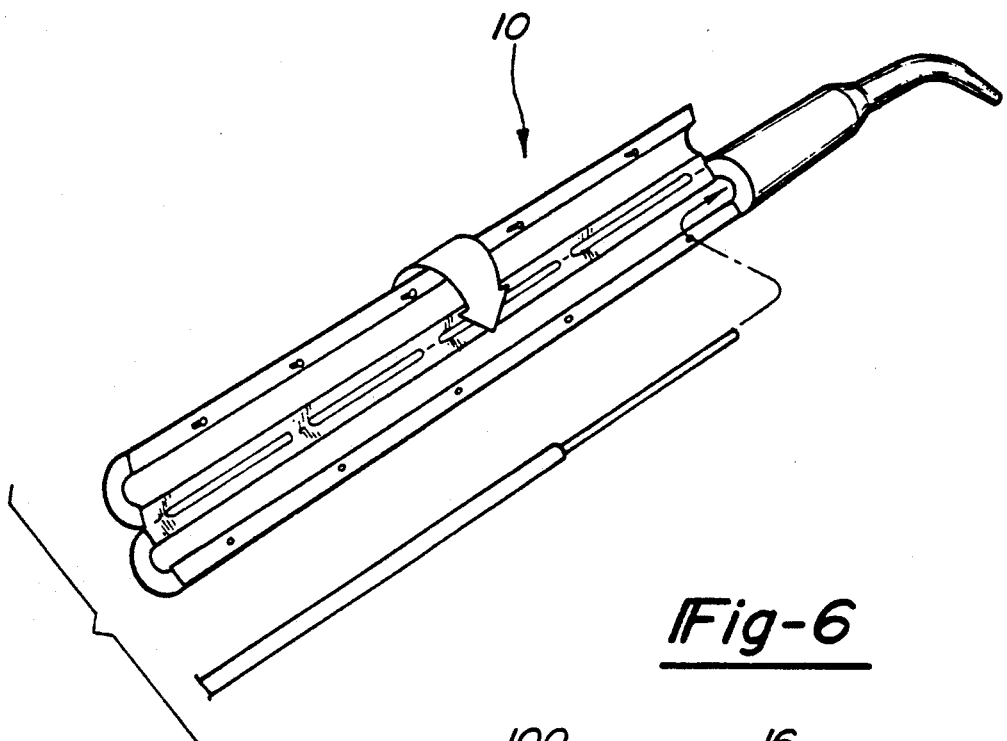
FIG. 6 is an elevational view showing a modification of the invention.

With reference first to FIG. 1, a preferred embodiment of the handpiece 10 of the present invention is thereshown for use with a dental laser assembly 12. The dental laser assembly 12 typically comprises a housing 14 in which the laser is contained. An elongated optical fiber assembly 16 has a proximal end 18 which receives the radiation from the laser (not shown) and discharges the laser radiation from its distal end 20 toward the target site. The optical fiber assembly itself includes an optical fiber strand 17 (FIG. 4) which is encased in an outer protective sheathing 19 (FIG. 4).

With reference now particularly to FIG. 2, the distal end 20 of the optical fiber strand 17 protrudes outwardly from end 22 of the handpiece 10. Furthermore, the handpiece 10 is elongated and is dimensioned to fit within the hand of the dentist.

With reference now especially to FIG. 3, an exploded sectional view of the handpiece 10 is thereshown. The handpiece 10 includes an elongated cylindrical body 24 having a throughbore 26. This throughbore 26, furthermore, is slightly larger in diameter than the outside diameter of the sheathing 19 for the optical fiber assembly 16 so that the optical fiber assembly 16 can be slidably positioned through the throughbore 26.

Still referring to FIG. 3, at least one, and preferably several longitudinally extending slots 28 are provided at one end 30 of the body 24. This end 30 of the body 24 is preferably reduced in diameter and includes an externally threaded portion 32 immediately adjacent the slots 28. The purpose of the slots 28 and threaded portion 32 will be subsequently described.

Still referring to FIG. 3, the handpiece 10 further includes an elongated nut 34 having an internally threaded portion 36 which threadably engages the externally threaded portion 32 of the body 24. A cylindrical recess 38 in the nut 34 is dimensioned to fit around the slotted end 30 of the body 10 while a throughbore 40 is provided at the end of the nut 34 opposite from the internally threaded portion 36.

With reference now to FIGS. 3 and 4 the cooperation between the nut 40 and body 24 forms a means for locking the end 30 of the body 24 to the optical fiber assembly against longitudinal movement. More specifically, as shown in FIG. 4, with the optical fiber assembly 16 positioned through the nut bore 40 and into the body bore 26, the threaded portion 36 of the nut 34 threadably engages the threaded portion 32 of the body 24 in the conventional fashion. Upon tightening, the nut 34 compresses against the slotted end 30 of the body which simultaneously compresses the end 30 of the body 24 against the outer periphery of the sheathing 19 for the optical fiber assembly 16. Upon doing so, the nut 34, body 10 and optical fiber assembly 16 are locked against longitudinal movement with respect to each other. The handpiece 10, however, can be detached from the optical fiber 16 by merely loosening the nut 34 and withdrawing the optical fiber assembly 16 from the body throughbore 26.

Referring again especially to FIG. 3, a cylindrical recess 50 is provided at the end 52 of the body 24 opposite from its slotted end 30. An annular locking ridge 54 protrudes inwardly into the recess 50 adjacent the body end 52.

A cannula 56 has one end 58 which is insertable into the body recess 50. Furthermore, this end 58 of the cannula 56 includes an annular groove or indentation 60 which, upon insertion into the recess 50 to the position illustrated in FIG. 4, cooperates with the locking ridge 54 to lock the body 24 and cannula 56 together. Once the end 58 of the cannula 56 is inserted into the recess 50, the cannula 56 cannot be removed from the body 24 without destroying or at least severely damaging the cannula 56 and/or body 24.

The cannula 56 also includes a throughbore 62 which, upon assembly of the cannula 56 to the body 24, registers with the body throughbore 26. The cannula throughbore 62 has a diameter slightly greater than the diameter of the optical fiber strand 17. Consequently, the optical fiber strand 17 extends outwardly from a distal end 64 of the cannula 56 as shown at 66.

As shown in FIG. 2 and 3, the distal or free end 68 of the cannula 56 is formed at an oblique angle up to a perpendicular angle with respect to the longitudinal axis of the body 24. Preferably the cannula is formed by molding the cannula as a straight segment and then bending the cannula. This procedure increases the flexibility of manufacturing cannulas having different angles. In addition, as best shown in FIG. 3, the internal diameter of the cannula throughbore is reduced in the oblique portion 68 of the cannula 56 to a diameter just slightly greater than the diameter of the optical fiber strand 17 of the optical fiber assembly 16. Consequently, the end 72 of the sheathing 19 for the optical fiber assembly 16 is positioned either within the enlarged diameter portion of the cannula throughbore 62, or the body throughbore 26.

With reference now especially to FIGS. 2 and 5, a transparent longitudinally extending window 70 is provided along the body 24 so that the optical fiber assembly 16, as well as the end 72 of the optical fiber sheathing 19 can be viewed through the window 70. Hash marks 74 are also provided along the window 70 so that the dentist can detect any movement of the sheathing 19, and thus movement of the optical fiber assembly 16, which occurred during the dental procedure. Such movement could occur, for example, if the nut 34 were not tightly secured.

Still referring to FIG. 2, marks 76 are also provided at predetermined distances along the oblique end 68 of the cannula 56 and/or body. These marks 76 thus facilitate the use of the handpiece 10 in endontic and periodontal applications where the end 20 of the optical fiber is hidden during use and provides an indication of the depth of insertion of the cannula 56.

The entire handpiece 10 is constructed of an inexpensive material, such as plastic or polypropylene, and the entire handpiece 10 is discarded after each individual use. Furthermore, the handpiece 10 is preferably constructed of a non-autoclavable material so that sterilization and reuse of the handpiece 10 is not possible.

As an alternative material, the handpiece 10 is constructed of a plastic which melts at a relatively low temperature, for example, less than 160° F., so that sterilization of the handpiece is not possible.

Although the foregoing describes a preferred embodiment of our invention, other configurations are possible. For example, the body can be constructed from two longitudinally extending halves (FIG. 6) which are then secured together and entrap the optical fiber assembly between them.

Figure 7:
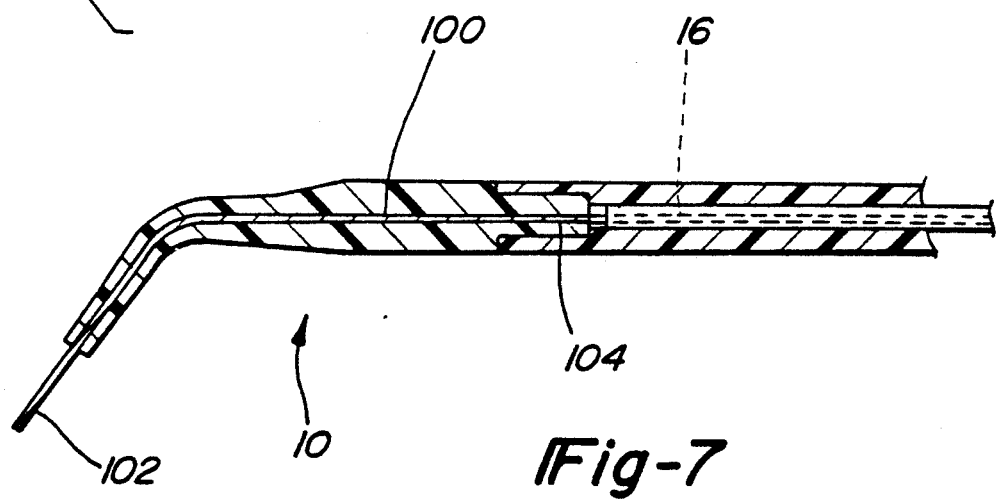
FIG. 7 is a sectional view illustrating still a further modification of the invention.

Alternatively, as shown in FIG. 7, the handpiece 10 can include an optical fiber segment 100 having one end 102 which protrudes outwardly from the handpiece 10 while the other end 104 of the segment is positioned at a midpoint in the handpiece 10. The distal end of the optical fiber assembly 16 is then detachably secured to the handpiece 10 so that the distal end of the optical fiber assembly 16 registers with the other end 104 of the segment 100 and transmits radiation through the segment and out through its end 102.

Having described our invention, however, many modifications thereto will become apparent to those skilled in the art to which it pertains without deviation from the spirit of the invention as defined by the scope of the appended claims.

We claim:

1. A dental device for use with a dental laser assembly of the type having a laser and an elongated optical fiber assembly, said optical fiber assembly having a proximal end which receives radiation from the laser and a distal end which delivers the laser radiation to a target site, said device comprising:
    an elongated handpiece, said handpiece being dimensioned to be held in an human hand,
    said handpiece having a longitudinal throughbore dimensioned to receive the optical fiber assembly so that the distal end of the optical fiber assembly extends outwardly from one end of the handpiece,
    means for removably locking said handpiece to said optical fiber assembly to prevent movement of said optical fiber assembly with respect to said handpiece,
    wherein said handpiece is constructed of a non-metallic material, said handpiece adapted to be disposed of after use on a single patient,
    wherein said locking means comprises means for compressing the other end of said handpiece against said optical fiber assembly,
    wherein said other end of said handpiece comprises at least one longitudinally extending slot which extends from an outer periphery of said handpiece to said throughbore, and wherein said compressing means comprises a nut which threadably engages said other end of said handpiece around said slot and which, upon tightening, compresses said slot and said handpiece around the optical fiber assembly.

2. The invention as defined in claim 1 wherein said handpiece is constructed primarily of a non-autoclavable material.

3. The invention as defined in claim 1 wherein said handpiece is constructed primarily of plastic.

4. The invention as defined in claim 3 wherein said plastic has a melting temperature of less than about 212° Fahrenheit.

5. The invention as defined in claim 1 and comprising longitudinally spaced indicia provided adjacent said one end of said handpiece.

6. The invention as defined in claim 1 and comprising means for enhancing mechanical gripping of said handpiece.

7. The invention as defined in claim 6 wherein said means for enhancing mechanical gripping of said handpiece comprises a textured portion provided on a portion of an outer surface of said handpiece.

8. The invention as defined in claim 1 wherein said handpiece is of a one piece construction.

9. The invention as defined in claim 1 wherein the optical fiber assembly extends substantially perpendicularly outwardly from the longitudinal axis of said handpiece.

10. A dental device for use with a dental laser assembly of the type having a laser and an elongated optical fiber assembly, said optical fiber assembly having a proximal end which receives radiation from the laser and a distal end which delivers the laser radiation to a target site, said device comprising:
an elongated handpiece, said handpiece being dimensioned to be held in an human hand,
said handpiece having a longitudinal throughbore dimensioned to receive the optical fiber assembly so that the distal end of the optical fiber assembly extends outwardly from one end of the handpiece,
means for removably locking said handpiece to said optical fiber assembly to prevent movement of said optical fiber assembly with respect to said handpiece,
wherein said handpiece is constructed of a non-metallic material, said handpiece adapted to be disposed of after use on a single patient,
wherein said handpiece comprises a longitudinally extending transparent window through which said optical fiber assembly is observable.

11. The invention as defined in claim 10 wherein a portion of said window is positioned adjacent said one end of said handpiece.

12. The invention as defined in claim 10 and comprising longitudinally spaced markings on said window.

13. A dental device for use with a dental laser assembly of the type having a laser and an elongated optical fiber assembly, said optical fiber assembly having a proximal end which receives radiation from the laser and a distal end which delivers the laser radiation to a target site, said device comprising:
an elongated handpiece, said handpiece being dimensioned to be held in an human hand,
said handpiece having a longitudinal throughbore dimensioned to receive the optical fiber assembly so that the distal end of the optical fiber assembly extends outwardly from one end of the handpiece,
means for removably locking said handpiece to said optical fiber assembly to prevent movement of said optical fiber assembly with respect to said handpiece,
wherein said handpiece is constructed of a non-metallic material, said handpiece adapted to be disposed of after use on a single patient,
wherein said handpiece comprises an elongated body and a cannula, said body and said cannula each having a longitudinally extending throughbore, means for attaching said body and said cannula together so that said cannula throughbore and said body throughbore register and form said handpiece throughbore,
wherein said attaching means comprises means for frictionally attaching said cannula and said body together and for preventing detachment of said body from said cannula without destruction of said handpiece.

14. The invention as defined in claim 13 wherein said cannula has one end which is insertable into one end of said body, and wherein said attaching means further comprises an annular groove on said cannula and a locking ridge on said body, said locking ridge engaging said annular groove upon insertion of said cannula into said body.

15. A dental device for use with a dental laser assembly of the type having a laser and an elongated optical fiber assembly, said optical fiber assembly having a proximal end which receives radiation from the laser and a distal end which delivers the laser radiation to a target site, said device comprising:
an elongated handpiece, said handpiece being dimensioned to be held in an human hand,
said handpiece having a longitudinal throughbore dimensioned to receive the optical fiber assembly so that the distal end of the optical fiber assembly extends outwardly from one end of the handpiece,
means for removably locking said handpiece to said optical fiber assembly to prevent movement of said optical fiber assembly with respect to said handpiece,
wherein said handpiece is constructed of a non-metallic material, said handpiece adapted to be disposed of after use on a single patient,
wherein said handpiece comprises an elongated body and a cannula, said body and said cannula each having a longitudinally extending throughbore, means for attaching said body and said cannula together so that said cannula throughbore and said body throughbore register and form said handpiece throughbore,
wherein said cannula includes an arcuately curved portion.

16. The invention as defined in claim 15 wherein said arcuately curved portion of said cannula is formed by molding said cannula as a straight segment and subsequently bending said arcuately curved portion of said cannula.

17. A dental device for use with a dental laser assembly of the type having a laser and an elongated optical fiber assembly, said optical fiber assembly having a proximal end which receives radiation from the laser and a distal end which delivers the laser radiation to a target site, said device comprising:
an elongated handpiece, said handpiece being dimensioned to be held in an human hand,
said handpiece having a longitudinal throughbore dimensioned to receive the optical fiber assembly so that the distal end of the optical fiber assembly extends outwardly from one end of the handpiece, means for removably locking said handpiece to said optical fiber assembly to prevent movement of said optical fiber assembly with respect to said handpiece, wherein said handpiece is constructed of a non-metallic material, said handpiece adapted to be disposed of after use on a single patient, wherein said handpiece comprises an elongated body and a cannula, said body and said cannula each having a longitudinally extending throughbore, means for attaching said body and said cannula together so that said cannula throughbore and said body throughbore register and form said handpiece throughbore, wherein the optical fiber assembly comprises an optical fiber and a protective sheathing which encases said optical fiber, and wherein said body throughbore has a diameter slightly greater than the diameter of said sheathing while said cannula throughbore has a diameter slightly greater than the diameter of the optical fiber.

18. A dental device for use with a dental laser assembly of the type having a laser and an elongated optical fiber assembly, said optical fiber assembly having a proximal end which receives radiation from the laser and a distal end which delivers the laser radiation to a target site, said device comprising:

an elongated handpiece, said handpiece being dimensioned to be held in an human hand, said handpiece having a longitudinal throughbore dimensioned to receive the optical fiber assembly so that the distal end of the optical fiber assembly extends outwardly from one end of the handpiece, means for removably locking said handpiece to said optical fiber assembly to prevent movement of said optical fiber assembly with respect to said handpiece, wherein said handpiece is constructed of a non-metallic material, said handpiece adapted to be disposed of after use on a single patient, means for enhancing mechanical gripping of said handpiece, wherein said means for enhancing mechanical gripping of said handpiece comprises an elastomeric sheath provided around at least a portion of said handpiece.

19. A dental device for use with a dental laser assembly of the type having a laser and an elongated optical fiber assembly, said optical fiber assembly having a proximal end which receives radiation from the laser and a distal end which delivers the laser radiation to a target site, said device comprising:

an elongated handpiece, said handpiece being dimensioned to be held in a human hand, said handpiece having a longitudinal throughbore dimensioned to receive the optical fiber assembly so that the distal end of the optical fiber assembly extends outward form one end of the handpiece, means for removably locking said handpiece to said optical fiber assembly to prevent movement of said optical fiber assembly with respect to said handpiece, wherein said handpiece is constructed of a mon-metallic material, said handpiece adapted to be disposed of after use on a single patient, wherein said handpiece comprises an elongated body and a cannula, said body and said cannula each having a longitudinally extending throughbore, means for attaching said body and said cannula together so that said cannula throughbore and said body throughbore register and form said handpiece throughbore, wherein said body comprises a first longitudinally extending half and a second longitudinally extending half, and means for securing said halves together so that one side of said first half abuts against one side of said second half, said optical fiber assembly being entrapped between said halves.

20. A dental device for use with a dental laser assembly of the type having a laser and an elongated optical fiber assembly, said optical fiber assembly having a proximal end which receives radiation from the laser and a distal end which delivers the laser radiation to a target site, said device comprising:

an elongated handpiece, said handpiece being dimensioned to be held in an human hand, said handpiece having a longitudinal throughbore dimensioned to receive the optical fiber assembly so that the distal end of the optical fiber assembly extends outwardly from one end of the handpiece, means for removably locking said handpiece to said optical fiber assembly to prevent movement of said optical fiber assembly with respect to said handpiece, wherein said handpiece is constructed of a non-metallic material, said handpiece adapted to be disposed of after use on a single patient, wherein said handpiece comprises an elongated body and a cannula, said body and said cannula each having a longitudinally extending throughbore, means for attaching said body and said cannula together so that said cannula throughbore and said body throughbore register and form said handpiece throughbore, wherein said cannula has one end which is insertable into one end of said body, and wherein said attaching means further comprises an annular groove on said body and a locking ridge on said cannula, said locking ridge engaging said annular groove upon insertion of said cannula into said body.

* * * * *